(12) United States Patent
Del Negro et al.

(10) Patent No.: US 10,081,784 B2
(45) Date of Patent: Sep. 25, 2018

(54) PROCESS FOR THE CONTINUOUS ON-SITE PRODUCTION OF PERCARBOXYCILIC ACID SOLUTIONS AND DEVICE FOR ITS IMPLEMENTATION

(71) Applicant: Eltron Research & Development, LLC, Boulder, CO (US)

(72) Inventors: Andrew Del Negro, Broomfield, CO (US); Paul Grimmer, Longmont, CO (US)

(73) Assignee: Eltron Research & Development, LLC, Boulder, CO (US)

(*) Notice: Subject to any disclaimer, the term of this patent is extended or adjusted under 35 U.S.C. 154(b) by 152 days.

(21) Appl. No.: 15/154,595

(22) Filed: May 13, 2016

(65) Prior Publication Data

US 2017/0327775 A1    Nov. 16, 2017

(51) Int. Cl.
    *C11D 3/39*      (2006.01)
    *B01J 19/00*     (2006.01)
    *B01J 4/00*      (2006.01)
    *B01J 4/02*      (2006.01)

(52) U.S. Cl.
    CPC .............. *C11D 3/3945* (2013.01); *B01J 4/008* (2013.01); *B01J 4/02* (2013.01); *B01J 19/0006* (2013.01); *B01J 2219/00164* (2013.01); *B01J 2219/00177* (2013.01)

(58) Field of Classification Search
    CPC ..................................................... C11D 3/3945
    See application file for complete search history.

(56) References Cited

U.S. PATENT DOCUMENTS

| | | | |
|---|---|---|---|
| 3,432,546 | A | 3/1969 | Oringer et al. |
| 6,028,104 | A | 2/2000 | Schmidt et al. |
| 2007/0274857 | A1 | 11/2007 | Okano et al. |
| 2009/0314652 | A1 | 12/2009 | Buschmann et al. |
| 2014/0135394 | A1 | 5/2014 | Buschmann et al. |

FOREIGN PATENT DOCUMENTS

EP    2857491 A1    4/2015

*Primary Examiner* — Peter F Godenschwager
(74) *Attorney, Agent, or Firm* — Glenn G. Lenzen; Dietze and Davis, P.C.

(57) ABSTRACT

Provided are various methods and systems for producing peroxycarboxylic acid compositions, and in particular, non-equilibrium compositions of peracetic acid. The methods and systems control flow rates and proportions of feedstocks/reactants, perform the required sequence of reaction steps to produce high yield peroxycarboxylic acid solutions in a continuous manner, and provide optimal reaction time and reactant mixing for continuous and safe on-site production.

9 Claims, 2 Drawing Sheets

PROCESS FOR THE CONTINUOUS ON-SITE PRODUCTION OF PERCARBOXYCILIC ACID SOLUTIONS AND DEVICE FOR ITS IMPLEMENTATION

FIELD OF THE INVENTION

The present invention relates to methods and systems for the continuous production of nonequilibrium solutions containing biocidal concentrations of certain acids. More specifically, the present invention relates to methods and systems for producing nonequilibrium solutions containing biocidal concentrations of peroxycarboxcylic acids, including peracetic acid, on-demand and at the point-of-use.

BACKGROUND OF THE INVENTION

Peracetic acid (PAA) is a strong disinfectant with a wide spectrum of antimicrobial activity. PAA is conventionally prepared by reaction of concentrated acetic acid (AA) and concentrated hydrogen peroxide (HP). Strong, homogeneous acidic catalysts (e.g. 1-20% sulfuric acid) are usually used to catalyze the reaction toward equilibrium. The reactants are supplied to a reactor and are mixed and converted to product mixture within the reactor. These mixtures are prepared in large quantities at a plant and after reaction, placed in storage or shipping containers and allowed to "cure" for several days during which time the mixture approaches and reaches steady state equilibrium. Because these mixtures are stored and shipped after the PAA formation reaction has reached equilibrium, they are referred to as "equilibrium mixtures".

The equilibrium PAA mixtures are typically prepared in concentrations between 5-35% (wt) PAA containing excess HP and AA with water making up the balance, i.e., high concentrations of HP and/or AA relative to PAA concentration. Stabilizers must be added to the equilibrium PAA to prevent decomposition during storage and transport to end-users. Major uses of equilibrium PAA include disinfection, bleaching and chemical synthesis. Current practice for such applications is distribution of bulk equilibrium PAA solutions from large manufacturing plants to locations of end-use, often involving multiple distributors and transport events. These solutions must be shipped in compliance with regulations for hazardous materials (corrosive, oxidizer) and are explosive. After delivery to the end-user, the equilibrium PAA is typically stored in vented drums until use. PAA concentrations up to 15% are typically used for water treatment, for sanitizing, disinfecting, and sterilizing in the food and beverage industry, in laundries and for medical applications. Higher PAA concentrations up to 40% are exclusively used for oxidation reactions.

In aqueous solution peracetic acid is in a chemical equilibrium with acetic acid, hydrogen peroxide and water. This equilibrium is represented in the following Equation (1):

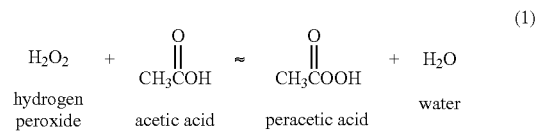

Accordingly, a higher concentration of reactants is required to produce a higher concentration of peracetic acid. Conversely, a higher concentration of water will drive the reaction backwards, which means dilute solutions have very low PAA equilibrium concentrations and mostly contain water and unused starting materials.

The molar concentration ratio of products versus reactants gives an equilibrium ratio often referred to as the equilibrium constant. Equilibrium constants for solutions of peroxycarboxylic acids can be determined by common methods. The equilibrium constant of a peroxycarboxylic acid can be determined by the following Equation (2A):

$$\frac{[RCO-O-OH] \times [H_2O]}{[RCO-OH] \times [H_2O_2]} = \text{equilibrium constant} \qquad (2A)$$

The equilibrium constant of PAA can be determined by the following Equation (2B):

$$\frac{[CH_3\overset{O}{\overset{\|}{C}}OOH] \times [H_2O]}{[CH_3\overset{O}{\overset{\|}{C}}OH] \times [H_2O_2]} = \text{equilibrium constant} \qquad (2B)$$

For equilibrium peracetic acid solutions this equilibrium constant typically ranges between 1.8 and 2.5 (D. Swern, ed., *Organic Peroxides*, Wiley-Interscience, New York, 1970-72).

An example of typical equilibrium compositions commercially produced and distributed in bulk is 5-35% by weight peracetic acid, up to 30% hydrogen peroxide, up to 40% acetic acid and the balance being water. The weight ratio of hydrogen peroxide to peracetic acid to acetic acid in the merchant products ranges between 4.6:1:1.3 (5-6% PAA equilibrium product) and 1:5.4:6.2 (35% PAA equilibrium product). Using only the $[H_2O_2]$:[PAA] ratio is an oversimplified definition for distinguishing equilibrium from non-equilibrium peracetic acid solutions in that it does not represent the acetic acid constituent involved with the equilibrium constant.

There is a large investment cost associated with the production of equilibrium PAA mixtures in a centralized plant, due to the high materials and equipment cost. The extended time needed for reaction to reach equilibrium is a further limitation. Practical production of the equilibrium mixtures requires the use of a catalyst which then needs to be separated from the product by costly purification steps. To minimize the impact of shipping costs, the equilibrium mixtures are produced at relatively high concentrations and then diluted at the point-of-use. However, these mixtures are hazardous and explosive and require costly shipping and handling procedures. The shipping volume is limited to less than 300 gallons per container due to the hazardous nature of the equilibrium mixtures, creating challenging and costly logistics for large volume end-users. The abovementioned issues result in a PAA product mixture that is more costly to the end-user, as well as more dangerous than embodiments of the present invention.

It is possible to produce PAA on-site. Large quantities of equilibrium PAA can be produced by blending concentrated hydrogen peroxide and acetic acid in water. Sulfuric acid may also be added as a catalyst to accelerate the equilibration. The blended solution is allowed to 'cure' for at least 6-10 days while reaching chemical equilibrium prior to use.

The cure time increases with decreasing concentration of either starting material and is several weeks or longer at very low point-of-use concentrations. Most applications using peracetic acid (with the exception of pulp bleaching) are regulated to use less than 170 mg/L concentrations for hard surface cleaning and less than 80 mg/L for contact with produce and often less than 10 mg/L for water treatment.

As an example of the drawback to producing low concentration equilibrium solutions, a 200 mg/L concentration of peracetic acid in an equilibrium solution would contain 4000 mg/L hydrogen peroxide and 35,000 mg/L acetic acid that is unused starting material (equilibrium constant=2.05). In contrast, nonequilibrium peracetic acid solutions can contain 200 mg/L peracetic acid, 200 mg/L hydrogen peroxide and 160 mg/L acetic acid (equilibrium constant=9315). Therefore to directly produce low concentrations of peracetic acid rapidly and economically on-site, a nonequilibrium product is required.

"Nonequilibrium" refers to chemical mixtures that do not provide a determined equilibrium constant value, such as those determined by Equation (2A) for peroxycarboxylic acids in general, or by Equation (2B) for peracetic acid solutions. Accordingly, a nonequilibrium PAA solution is optionally described as having an equilibrium constant typically as calculated by Equation (2) that is not between 1.8 and 2.5.

Conventional nonequilibrium peracetic acid solutions are commercially produced in bulk by first producing equilibrium PAA, followed by distillation of such equilibrium PAA. The nonequilibrium distillate must then be stored near its freezing point to minimize decomposition and reequilibration during storage. This method of producing nonequilibrium peracetic acid is not practical for on-site end-users due to the complexity of such a production process, the operating skill required, the use of concentrated hazardous materials, and the explosion hazard created by distillation of concentrated peroxides.

To address some of these challenges, there have been various attempts to make solutions of PAA on-site, at the point-of-use. Equilibrium mixtures can be produced on-site by continuous production of a mixture of the individual components of equilibrium PAA (U.S. Pat. No. 6,719,921). The slow rate of reaction to equilibrium requires the use of a strong acid catalyst and therefore the catalyst is present in the product mixture. The reaction of individual components to form the equilibrium occurs in a reaction vessel with enough volume to give the reaction mixture enough residence time to reach equilibrium. This may lead to increased and impractical startup times in the event of planned or unplanned system shutdowns. The nature of the equilibrium mixture means that there is inherently some proportional quantity of reactants (HP and AA) left in the product mixture. This equilibrium reaction utilizes the feedstocks (HP and AA) in a less efficient manner than the irreversible and rapid reaction to produce nonequilibrium mixtures in embodiments of the present invention. The rapid reaction in embodiments of the present invention minimizes the system startup time making it more suitable for on-demand production of PAA at the point-of-use.

Reactive precursor mixtures can be reacted with a stream of alkali metal hydroxide to produce nonequilibrium PAA mixtures at the point-of-use. U.S. Pat. Appln. Pub. No. 20120245228 describes a premixed stream of acetyl donor and hydrogen peroxide reacted with a stream of sodium or potassium hydroxide. The alkaline environment allows for the perhydrolysis reaction of peroxide, producing nonequilibrium PAA mixtures. This process is difficult to control due to the instability of the reactive precursor mixture, as well as the heterogeneity of the precursor mixture, and is less efficient (in terms of % yield) compared to embodiments of the present invention. The lower yield results in a PAA composition with increased acetic acid compared to embodiments of the present invention. The costs associated with preparing the precursor mixture as well as the lower PAA yield for the reaction result in a more costly PAA mixture than embodiments of the present invention.

U.S. Pat. No. 5,505,740 describes a method for in-situ formation of peroxyacid using peracid precursor, a source of hydrogen peroxide and a source for delayed release of acid for a bleaching product (wash solution) and a method of removing soil from fabrics. In the method of Kong et al. the aqueous wash solution is initially raised to a relatively high pH level (e.g., 9.5) to enhance production of the peroxyacid in the aqueous solution, followed by lowering the pH of the aqueous solution by, for example, the delayed release of acid, to enhance bleach performance. The source of the delayed release of acid may be an acid of delayed solubility, an acid coated with a low solubility agent or an acid generating species, or an acid independent of the bleaching product employed.

British Pat. Pub. No. GB 1,456,592 relates to a bleaching composition having both encapsulated bleaching granules and agglomerated pH-adjustment granules acid. The bleaching granules comprise an organic peroxy acid compound stabilized by salt(s) of strong acids and water of hydration, encapsulated in a fatty alcohol coating. The pH-adjustment granules comprise a water-soluble alkaline buffer yielding pH 7-9 agglomerated with a suitable adhesive material to yield the desired solubility delay. Preferred peroxy acid compounds are diperisophthalic acid, diperazelaic acid, diperadipic acid, monoperoxyisophthalic acid, monosodium salt of diperoxyterephthalic acid, 4-chlorodiperoxyphthalic acid, p-nitroperoxy benzoic acid, and m-ehloroperoxy benzoic acid.

U.S. Pat. No. 6,569,286 and published PCT Pub. No. WO 0019006 (App. No. WO1999GB03178) relate to a process for bleaching of wood and non-wood pulp. In this process an agglomerate containing, among others, a bleach activator (e.g., tetraacetylethylenediamine, TAED) and a peroxide soluble binder (e.g., polyvinyl alcohol) is added to a dilute solution of hydrogen peroxide. The components are allowed to react and the pH of the resulting mixture is chemically adjusted to a suitable alkaline pH and the pulp is contacted with the resulting solution.

Peracids can be produced in electrochemical cells or reactors by establishing a potential difference across electrodes immersed in electrically-conducting fluid and introducing appropriate reactant materials. For example, U.S. Pat. No. 6,387,238 relates to a method for preparing an antimicrobial solution containing peracetic acid in which hydrogen peroxide or peroxide ions are formed electrolytically and the hydrogen peroxide or peroxide ions are then reacted with an acetyl donor to form peracetic acid.

U.S. Pat. No. 6,949,178 discloses a process and apparatus for the preparation of peroxyacetic acid at the cathode of an electrolytic cell having an ionically conducting membrane in intimate contact between an anode and a gas diffusion cathode. The method comprises supplying an aqueous organic acid solution to the anode, supplying a source of oxygen to the cathode, and generating peroxyacid at the cathode.

European Patent EP1469102 discloses the process and apparatus for electrolytically producing peracetic acid from acetic acid or acetate using an electrolytic cell incorporating a gas diffusion electrode in the presence of a solid acid catalyst.

JP-T-2003-506120 discloses the electrolytic synthesis of peroxyacetic acid. In this method, oxygen gas is electrolyzed to obtain peroxide species which are then reacted with acetylsalicylic acid to obtain the peroxyacetic acid.

Other disadvantages of known methods are, among others, (1) the long reaction or cure times required to produce equilibrium concentrations of peracetic acid solutions; (2) costs of shipping, handling, and storage, (3) limited shelf life of concentrated acids, bases, and peroxides, which are all corrosives and hazardous materials; (4) cost of shipping large quantities of water containing merchant hydrogen peroxide; (5) the presence of stabilizers or contaminants originating from merchant hydrogen peroxide; and (6) relatively low production rates or excessive equipment size and cost. In addition, the practice of combining bulk chemical constituents obtained from merchant suppliers to produce nonequilibrium peroxycarboxylic acid solutions, including peracetic acid, does not produce the compositions provided herein. Processes and related devices provided herein eliminate these disadvantages and other disadvantages associated with shipping, storing and handling concentrated merchant peracetic acid.

A process that mixes reactants with fewer storage or shipping requirements than the product solution, rapidly and safely, to provide the benefits of a nonequilibrium solution of a peroxycarboxylic acid and the benefits of on-site mixing with a high yield would be advantageous. The process to efficiently produce continuous nonequilibrium PAA requires manipulating and reacting the feedstocks in a particular sequence and maintaining specific ratios to prevent the accidental formation of unsafe mixtures and to maintain proportional flow of feedstock reactants to ensure optimal reaction conversion, and thereby, economic PAA production.

Consequently, there is a need for an efficient process of preparing peroxycarboxylic acids, including peracetic acid, on-site, on-demand, and cost-effectively. Other objectives may appear herein.

SUMMARY OF EMBODIMENTS OF THE INVENTION

The stated problems and other needs in the art as are apparent from the further description can be achieved by the process according to the methods and systems of embodiments of the present invention. Production at the point-of-use negates many of the costs and safety liabilities associated with transporting bulk equilibrium peroxycarboxcylic acid mixtures. The methods and systems are low-cost and simple, allowing the nonequilibrium peroxycarboxcylic process to occur at the point-of-use by the end-users of the nonequilibrium peroxycarboxcylic mixtures. The system controls flow rates, proportions of reactants, and the required sequence of reaction steps to produce high yield peroxycarboxcylic acid solutions in a continuous manner, and provides optimal reaction time, reactant stream proportions, mixed stream pH, and reactant mixing for continuous and safe on-site production.

Embodiments of the invention provide improved methods of production of nonequilibrium peroxycarboxylic acids and solutions containing nonequilibrium peroxycarboxylic acid for various applications. The invention also provides improved compositions comprising nonequilibrium peroxycarboxylic acids made by the methods herein. The methods and compositions herein are particularly useful for preparation of nonequilibrium peracetic acid (PAA) solutions. PAA is a representative peroxycarboxylic acid. Methods and compositions herein which are exemplified with PAA can be practiced in general with any one or more peroxycarboxylic acids.

The invention provides a method of producing nonequilibrium peracetic acid that facilitates on-site and on-demand production of PAA and that has many advantages over prior methods and compositions.

Various processes for producing nonequilibrium peroxycarboxylic acids, such as nonequilibrium peracetic acid are provided. The production is particularly useful for on-site production of nonequilibrium peracetic acid. Generally in embodiments of the present invention nonequilibrium PAA is produced by reacting a properly chosen acyl donor, preferably acetyl donor, with hydrogen peroxide to produce nonequilibrium peroxycarboxylic acid. The composition of the acetyl donor source for use in a commercial reactor system may be composed of an acetyl donor compound, optionally containing more than one type of acetyl donor compound, optionally containing an electrolyte salt, optionally containing a peroxide stabilizer, optionally containing a base, optionally containing an acid, optionally containing a solvent (water, alcohols, organic). The acyl or acetyl donor is chosen so that that the reverse reaction is not possible or has a very slow rate. Thus, acetic acid (or other carboxylic acid) itself is not a preferred acetyl donor. Examples of acetyl donors include, but are not limited to, O-acetyl donors (—O—C(O)CH$_3$), such asacetin, diacetin, triacetin, acetylsalicylic acid, (β)-D-glucose pentaacetate, cellulose (mono and tri) acetate, D-mannitol hexaacetate, sucrose octaacetate, and acetic anhydride. N-acetyl donors (—N—C(O) CH$_3$) may also be used, such as N,N,N'N'-tetraacetylethylenediamine (TAED), N-acetyl glycine, N-acetyl-5 DL-methionine, 6-acetamidohexanoic acid, N-acetyl-L-cysteine, 4-acetamidophenol, and N-acetyl-Lglutamine.

The solutions produced, including peracetic acid solutions, have nonequilibrium compositions, such as characterized by high peroxycarboxylic acid (POA) and water to carboxylic acid (CA) and hydrogen peroxide ($H_2O_2$) ratios. In an aspect, the ratio of [POA][$H_2O$]/[CA][$H_2O_2$] is ≥10, ≥100, ≥1000, ≥10,000. In another aspect the ratio of [POA]: [$H_2O_2$] is: ≥1, ≥5, ≥10, ≥100, when the [POA]:[CA] concentration ratio is ≥1.

More specifically, peracetic acid solutions of this invention have nonequilibrium compositions such as characterized by high peracetic acid (PAA) and water ($H_2O$) to acetic acid (AA) and hydrogen peroxide ($H_2O_2$) ratios. In an aspect, the ratio of [PAA][$H_2O$]/[AA][$H_2O_2$] is ≥10, ≥100, ≥1000, ≥10,000. In another aspect the ratio of [PAA]:[$H_2O_2$] is: ≥1, ≥5, ≥10, ≥100 when the [PAA]:[AA] concentration ratio is ≥1. The nonequilibrium PAA solutions are economically competitive to equilibrium peracetic acid solutions commercially produced ("merchant") and having typically maximum weight peracetic acid content of between 5% and 35%, where [PAA][$H_2O$]/[AA][$H_2O_2$] ratios are typically between 1.8 and 2.5.

A particular advantage of the use of nonequilibrium peroxycarboxylic acid is that solutions having concentrations of less than about 10 g/L peroxycarboxylic acid can be produced economically. This is particularly the case with nonequilibrium PAA. For example, making dilute solutions (<10 g/L) of equilibrium PAA is not cost-effective because in dilute solutions equilibrium favors the formation of hydrogen peroxide and acetic acid over PAA requiring high ratios of feed chemicals to obtain the desired PAA product at low concentration. Therefore, the cost of feed chemicals is much lower for nonequilibrium PAA relative to equilibrium PAA at low concentrations of PAA. Another advantage of nonequilibrium peroxycarboxylic acid is that the feed chemicals (hydrogen peroxide and acyl donor (or acetyl donor)) are significantly less hazardous than those of high concentration equilibrium solutions. This results in safer storage and handling for the end user.

One aspect of this invention provides for producing a nonequilibrium peroxycarboxylic acid solution by a process comprising:

a. diluting aqueous hydrogen peroxide solution with softened or deionized water to a concentration less than 10% (w/w), preferably less than 6% (w/w)

b. adding alkali metal hydroxide or alkali earth metal hydroxide, or solutions of alkali metal hydroxide or alkali earth metal hydroxide to adjust the pH of the resulting peroxide mixture to between 10 to 13.5.

c. thirdly adding a suitable O-acetyl or N-acetyl donor such that the ratio of peroxide to acetyl group in the reaction mixture is at least 1, more preferably 1.5 or greater.

d. mixing the components sufficiently and for a sufficient time for the two phase mixture to change into a single phase solution, indicating a nearly complete reaction e. optionally adding an acid source to the reacted mixture to adjust the mixture pH f. optionally adding additional peroxide to the reacted mixture to augment the mixture's peroxide component.

The foregoing has outlined rather broadly the features and technical advantages of embodiments of the present invention in order that the detailed description of embodiments of the invention that follows may be better understood. The above and other embodiments and features of this invention will be still further apparent from the description, the accompanying drawings, and/or the appended claims. Additional features and advantages of embodiments of the invention will be described hereinafter that form the subject of the claims. It should be appreciated by those skilled in the art that the conception and the specific embodiments disclosed may be readily utilized as a basis for modifying or designing other structures for carrying out the same purposes of embodiments of the present invention. It should also be realized by those skilled in the art that such equivalent constructions do not depart from the spirit and scope of embodiments of the invention as set forth in the appended claims.

BRIEF DESCRIPTION OF THE DRAWINGS

The drawings, which are incorporated herein, illustrate one or more embodiments of the present invention, thus helping to better explain one or more aspects of the one or more embodiments. As such, the drawings are not to be construed as limiting any particular aspect of any embodiment of the invention. In the drawings.

DETAILED DESCRIPTION OF THE INVENTION

Figure 1:
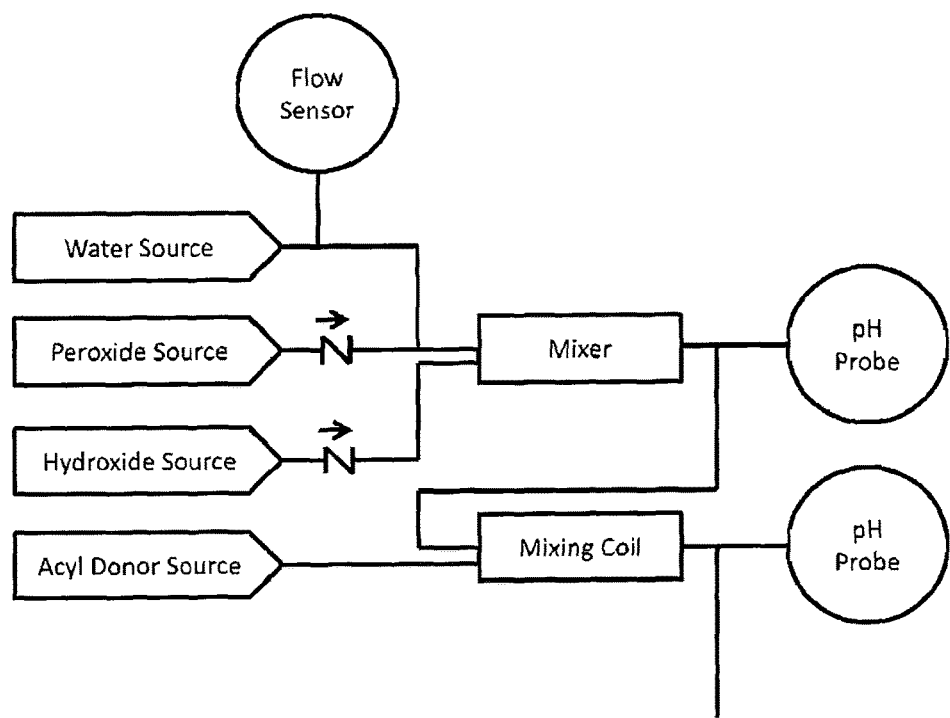
FIG. 1 is a flow diagram of the flow path of feedstock sources and control system components in an embodiment of the device in which water, peroxide source, hydroxide source, and acyl donor source are mixed in a specific order to produce a peroxycarboxylic acid solution with a controlled peroxycarboxylic acid concentration at the outlet.

The order of elements in this sequence, the concentrations described, the values of pH, the mixing conditions, and the concentration ratios described herein and controlled by the described system are unique features of embodiments of the present invention, enabling the rapid, safe, and economical on-site production of nonequilibrium peroxycarboxylic acid solutions by the system. Dilution of either the peroxide to less than 10% (w/w) with water prior to mixing with a source of hydroxide, or alternatively, the source of hydroxide prior to mixing with a source of peroxide, prevents formation of an explosive mixture and is therefore important for the safe operation of the system. The adjustment of pH of the peroxide solution to within the range of 10 to 13.5 prior to addition of the acyl donor causes the peroxycarboxylic acid formation reaction to proceed at a higher rate than at pH values outside this range. However, the rate of the decomposition reaction of the peroxycarboxylic acid increases with increasing pH. Control of pH prevents the decomposition reaction from limiting yield. Rapid formation of the peroxycarboxylic acid is desirable for on-demand applications. When the ratio of peroxide to acyl group in the reaction mixture is at least 1, the sequence produces peroxycarboxylic acids with the most efficiency with regard to conversion of starting materials. Efficient conversion of starting materials is desirable for economical production of peroxycarboxylic acids.

The pH of the reacted mixture exiting from the mixing mechanism, measured by a pH probe in the system, may not be at the desired pH for a given application. Therefore, acid or hydroxide sources may be added to the mixture prior to dispensing, to adjust the pH to make the dispensed solution suitable for a given application. In a similar manner, a peroxide source may be added to the mixture prior to dispensing, to increase the ratio of peroxide to peroxycarboxylic acid to be suitable for a given application.

As used herein, the term "about" modifying the quantity of an ingredient or reactant of embodiments of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and similar. The term "about" also encompasses amounts that differ due to different equilibrium conditions for a composition resulting from a particular initial mixture. Whether or not modified by the term "about", the claims include equivalents to the quantities.

As used herein, "comprising" is synonymous with "including," "containing," or "characterized by," and means the presence of the stated features, integers, steps, or components as referred to in the claims, but it does not preclude the presence or addition of one or more other features, integers, steps, components or groups thereof. The term is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The broad term comprising is intended to encompass the narrower consisting essentially of and the even narrower consisting of. Thus, in any recitation herein of a phrase "comprising one or more claim element" (e.g., "comprising A and B), the phrase is intended to encompass the narrower, for example, "consisting essentially of A and B" and "consisting of A and B." Thus, the broader word "comprising" is intended to provide specific support in each use herein for either "consisting essentially of" or "consisting of." The invention illustratively described herein suitably may be practiced in the absence of any element or elements, limitation or limitations which is not specifically disclosed herein.

As used herein, the term "peracid" is synonymous with peroxyacid, peroxy acid, percarboxylic acid and peroxoic acid. As is commonly known, peracid includes peracetic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "Nonequilibrium" refers to chemical mixtures that do not provide equilibrium constant value, such as those determined by Equation (2A) for peroxycarboxylic acids in general, or by Equation (2B) for peracetic acid solutions. Accordingly, a nonequilibrium PAA solution is optionally described as having an equilibrium constant typically as calculated by Equation (2) that is not between 1.8 and 2.5. In an aspect, the nonequilibrium PAA is defined as those solutions having an equilibrium constant of greater than 10, greater than 100, greater than 1000, and greater than 10,000. As used herein, in certain aspects "nonequilibrium peracetic acid solutions" refer to PAA solutions having equilibrium constants greater than 10, greater than 100, greater than 1000, and greater than 10,000.

"Acyl donor" refers to a material which supplies an acyl donor for reacting with the hydrogen peroxide or peroxide ions to form a solution which includes a peroxycarboxylic acid. In a specific embodiment, an "acyl donor" refers to a material which supplies an acetyl donor for reacting with the hydrogen peroxide or peroxide ions to form a solution which includes peracetic acid. "Acetyl donor" refers to a material which supplies an acetyl donor for reacting with the hydrogen peroxide or peroxide ions to form a solution which includes a peroxycarboxylic acid. In an embodiment, an acetyl donor refers to a material which supplies an acetyl donor for reacting with the hydrogen peroxide or peroxide ions to form a solution which includes peracetic acid.

As used herein, "sufficient mixing" means mixing that causes a two-phase mixture of acyl donor and aqueous peroxide solution to become a one-phase flow within the residence time in the mixer or mixing tank. The residence time is defined as the volume flow rate of mixture entering the mixer or mixing tank with respect to time divided by the volume of the mixer or mixing tank.

The term "triacetin" is synonymous with glycerin triacetate; glycerol triacetate; glyceryl triacetate, 1,2,3-triacetoxypropane, 1,2,3-propanetriol triacetate and all other synonyms of CAS Registry Number 102-76-1.

Figure 2:
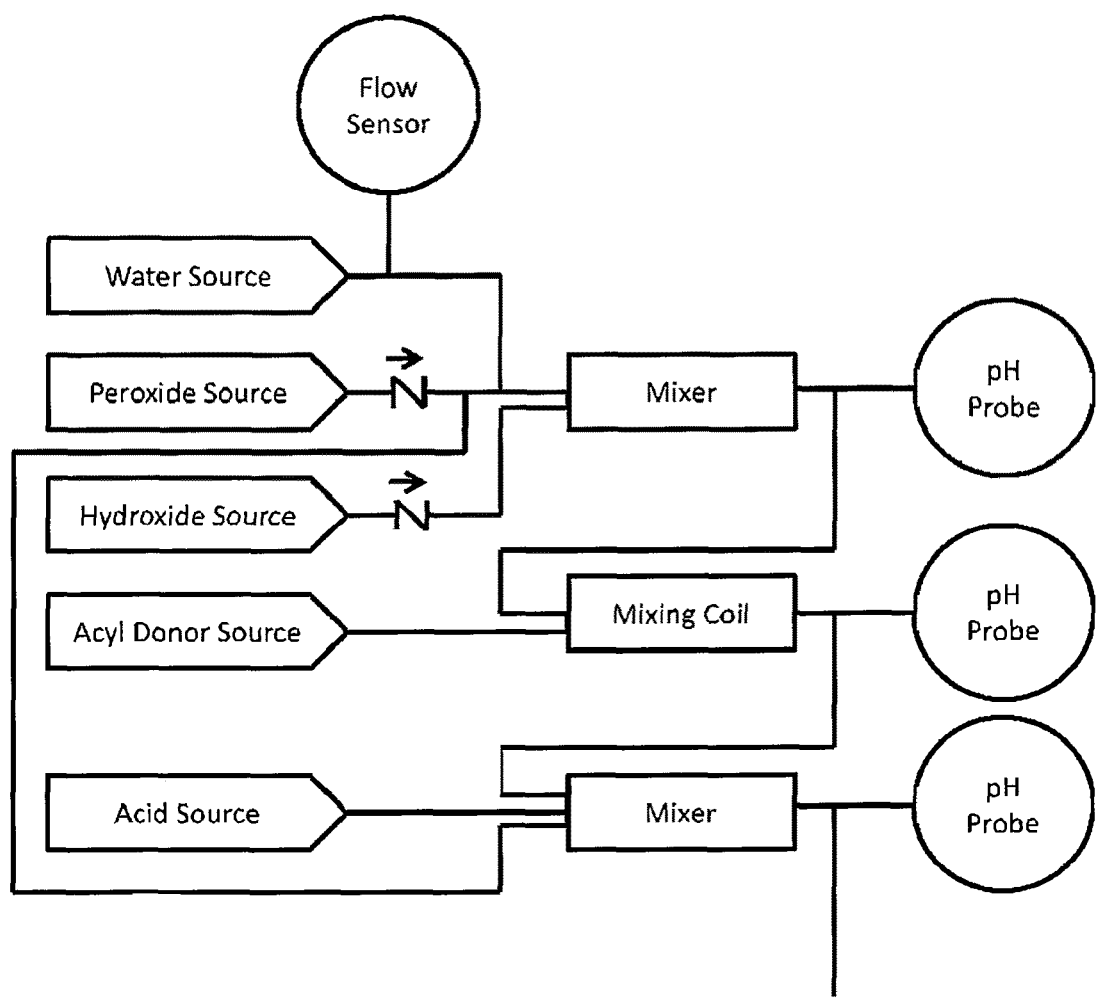
FIG. 2 is a flow diagram of the flow path of feedstock sources and control system components in an embodiment of the device in which water, peroxide source, hydroxide source, acyl donor source, and acid source are mixed in a specific order to produce peroxycarboxylic acid solution with a controlled pH, concentration of peroxycarboxylic acid, and concentration of peroxide at the outlet.

Flow-charts of exemplary processes of the invention for production of PAA are provided in FIGS. 1-2.

The product mixture is prepared by first diluting the HP feedstock to a concentration less than 10% (w/v) then adjusting the pH to 11.5-13.5 by addition of alkali metal hydroxide (preferably NaOH, or KOH) to maximize the ratio of —OOH to —OH in the reaction mixture. The pH at this step is also optimized to have enough alkalinity to result in a product mixture where pH remains above 9 after the base-consuming reactions are complete. The diluted, alkaline peroxide solution is then reacted with a suitable O-acetyl or N-acetyl peroxide activator. Preferably, the activator is non-toxic, non-flammable, and has kinetically rapid reactivity with peroxide. More preferably, peroxide activator is monoacetin, diacetin, or triacetin. The stoichiometry of —OOH to acetyl group is controlled to result in high selectivity for PAA production over acetic acid, or alternatively to result in a product mixture with a specified remaining peroxide concentration, which may be desirable for certain applications.

The ratio of —OOH to acetyl group is controlled to result in a product mixture with a specified remaining concentration of —OOH. For example, if that ratio is 1:1, there will be very little peroxide remaining in the product mixture. If the ratio of —OOH to —OH is 2:1 then after reaction, the mixture will have slightly more than 1-fold peroxide remaining after reaction. If the —OOH to —OH ratio is 10:1, there will be slightly more than 9-fold peroxide to PAA in the resulting peroxide mixture.

The chemical properties can be further manipulated after reaction by augmentation of peroxide, or pH adjustment by addition of acidic components, making the mixture more stable. Acids may include, but are not limited to, sulfuric acid, acetic acid, citric acid, nitric acid for food surface application, for example.

The reaction components may be combined in individual batches or may be combined using a continuous process.

Non-limiting alternate embodiments, procedures, or methods of construction, include addition of HP after the reaction; adjustment of the pH post reaction; intentional under-stoichiometry reaction between —OOH and acetyl group to produce a product with minimal HP in the product composition; and using peroxide activators other than triacetin.

SPECIFIC EXAMPLES

Example 1

88.2 mL of ~34% (w/w) hydrogen peroxide was diluted to 1000 mL in deionized water. The hydrogen peroxide concentration was determined to be 3.40% and the pH was 3.99. 100 ml of this diluted HP solution was placed in a 150 ml beaker equipped with a magnetic stir bar. NaOH (1.82 g) was added to the stirred solution, raising the pH to 12.51. Titration indicated the concentration of the alkaline peroxide solution to be 3.35%. To this solution, triacetin (3.09 ml, 2-fold excess HP to acetyl group) was added and the mixture was stirred vigorously for 10 min. After 10 min. the mixture pH had dropped to 10.64. The remaining concentration of HP was determined to 1.68% and the PAA concentration was 2.87%.

Example 2

88.2 mL of ~34% (w/w) hydrogen peroxide was diluted to 1000 mL in deionized water. The hydrogen peroxide concentration was determined to be 3.43% and the pH was 4.28. 100 ml of this diluted HP solution was placed in a 150 ml beaker equipped with a magnetic stir bar. NaOH (2.13 g) was added to the stirred solution, raising the pH to 12.48. Titration indicated the concentration of the alkaline peroxide solution to be 3.37%. To this solution, triacetin (3.1 ml, 2-fold excess HP to acetyl group) was added and the mixture was stirred vigorously for 10 min. After 10 min. the mixture pH had dropped to 11.23. The remaining concentration of HP was determined to 1.00% (w/w) and the PAA concentration was 3.06%.

Concentrated $H_2SO4$ (98%, 18.4 M) was added (1.5 ml) to the stirred mixture, dropping the pH to 3.01. The temperature of the mixture increased to 36° C. during pH adjustment. The concentration of hydrogen peroxide in the product was found to be 0.90% and the concentration of PAA was 2.74%.

Various types of mixing apparatus can be used in the practice of this invention. Several embodiments are considered that differ in the type of mixing mechanism used to mix the stream after the streams of the peroxide source, the hydroxide source, the acyl donor, and the diluting water are combined. A continuous mixing tank with agitation may be used, to which the components are added and from which the product stream is removed, continuously. In this embodiment, the product stream may contain unreacted components. Also, reactants are added to the tank containing a solution that is substantially the same as the desired product stream, in which the pH and reactant concentration ratios are not ideal for producing with the highest yield. The pH of the mixture contained in a small volume decreases as the reaction to form a peroxycarboxylic acid proceeds. Several approaches and apparatus may be used to carry out the mixing. Approaches include active mixing, passive mixing, induction, and injection methods. Apparatus effective in this invention include mechanically stirred tanks, centrifugal mixers, centrifugal pumps, static mixers, eductors, venturi mixers, and injector tubes and nozzles. Reaction components may be introduced to such apparatus by means of dosing pumps, metering pumps, peristaltic pumps, gravity feed, solenoid valve feed, rotary valve feed, and pressure driven feed mechanisms utilizing pneumatic or hydraulic driving forces. The mixture of alkaline hydrogen peroxide and acetyl or acyl donor is provided a reaction time (also called residence time or dwell time or cure time) in the mixing apparatus that allows the formation of the peroxyacetic acid product to occur. The reaction time is preferably adjusted to maximize peroxycarboxylic acid yield prior to pH adjustment, stabilization or use.

Alternatively, a batch mixing tank with agitation may be used, to which the components are added and from which the product stream is removed, after sufficient reaction time. In this embodiment, the product stream will contain fewer unreacted components and the pH and reactant concentration ratios will be close to those ideal for the best product yield. However, this embodiment may be impractical for an on-demand production application.

Alternatively, a series of mixing tanks, where the contents of each tank is continuously drained and used to fill the succeeding tank or removed as the product stream, may be used. In this embodiment, the conditions in each mixing tank will be closer to ideal for the stage of the reaction contained in each tank. The reactants in this embodiment may also move through the embodiment with an average flow rate that is practical for on-demand applications.

Another preferred mixing apparatus comprises a mixing vessel equipped with a mechanical stirrer. In this case, the mixing vessel continuously receives the feed streams of reactants, and either continuously or intermittently discharges a product mixture formed from these feed streams. The mechanical stirrer can be programmed to operate continuously or intermittently as long as the discharged product mixture is of desired composition. For instance, if the discharge is continuous, the system is designed and constructed such that the total incoming volume to the mixing vessel and the concurrent outgoing volume from the vessel remain equal and so that the vessel continuously contains a predetermined volume of contents which are being mixed by the mechanical stirrer. In such case, the stirrer preferably is operated continuously.

In one preferred embodiment the mixing apparatus comprises a static mixer. The static mixer can be of any suitable design and configuration as long as it is capable of continuously receiving the feed streams of reactants, and continuously discharging a product mixture formed from these feed streams that is substantially uniform in composition and/or satisfies product specifications.

Alternatively, a static mixer with sufficient volume relative to the volume flow rate to provide a sufficient reaction time may be used. The static mixer may consist of a mixer followed by a continuous tube reactor constructed from pipe or tube. This embodiment provides sufficient mixing and a continuous flow of reactants and product suitable for on-demand operation. In this embodiment, passing the mixed components through a mixer of suitable length and volume to ensure a residence time of the components within the mixer of sufficient time for the two-phase mixture to form into a single phase solution allows sufficient time for the peroxycarboxylic acid formation reaction to proceed mostly to completion, due to the plug nature of the flow of components in the mixer.

One unexpected benefit of the static mixer is a rapid reaction of the mixture to form peracetic acid when a mixing coil or small mixing tank is used instead of a large mixing tank, as would be used to store the daily product of the process. When the reaction was tested in small volume mixing containers at the bench scale, in batch mixtures, increased agitation of the mixture lead to faster reaction times. This is due to the low rate of dissolution of triacetin in the aqueous solution of peroxide and hydroxide. Increasing the agitation increases the homogeneity of the mixture, allowing greater surface area of the triacetin volume in the mixture, allowing a faster reaction rate. This benefit would be expected from correctly sized static mixers and tube reactors that provide sufficient agitation for bubbles of undissolved triacetin or other acyl donor to be small in size.

In another embodiment, the tube reactor may have two different diameters along its length. The first segment of the mixing coil that the mixture passes through has a smaller diameter and a more turbulent flow. This encourages thorough mixing of the mixture. The second segment of the mixing coil that the mixture passes through has a larger diameter, allowing the thoroughly mixed mixture sufficient time to react in a shorter distance of tubing.

In an embodiment, there is provided a method for producing non-equilibrium peroxycarboxylic acid comprising:

a. first diluting aqueous hydrogen peroxide solution with a dilute alkali metal hydroxide or alkali earth metal hydroxide solution to produce a mixture with a hydrogen peroxide concentration less than 10% (w/w), preferably less than 6% (w/w) and a pH between 10 and 13.5.

b. Next adding a suitable O-acetyl or N-acetyl donor such that the ratio of peroxide to acetyl group in the reaction mixture is at least 1, more preferably 1.5 or greater.

c. suitably mixing the components for sufficient time to allow complete reaction d. optionally adding additional dilute peroxide (<35% w/w) to the reacted mixture to augment the mixture's peroxide component e. optionally adding acid to the reacted mixture to adjust the mixture pH f. further diluting the mixture with either clean (softened or DI) water or process water to point-of-use biocide concentration.

In an embodiment, there is provided a method for producing non-equilibrium peroxycarboxylic acid with controlled ratio of peroxycarboxylic acid to peroxide and controlled pH, the method comprising:

a. Providing at least one feed stream comprising a non-equilibrium peroxycarboxcylic acid;

b. Supplying at least one source of aqueous peroxide to one or more of the at least one feed stream comprising a non-equilibrium peroxycarboxylic acid;

c. Supplying at least one source of acid or hydroxide to one or more of the at least one feed stream comprising a non-equilibrium peroxycarboxylic acid and/or the at least one source of aqueous peroxide;

d. Varying the volumetric flow rates of the streams of peroxycarboxylic acid, aqueous peroxide, and acid or hydroxide to provide the a peroxycarboxylic acid stream with the desired ratio of peroxycarboxylic acid to peroxide and the desired solution pH.

In an embodiment, there is provided a method for producing non-equilibrium peroxycarboxylic acid comprising:

a. Providing at least one source of water;

b. Providing at least one source of aqueous peroxide;

c. supplying one or more of the at least one source of water to one or more of the at least one source of aqueous peroxide to generate at least one source of dilute aqueous peroxide having a concentration of between 0.1% and 10%;

d. Providing at least one source of aqueous hydroxide;

e. supplying one or more of the at least one source of aqueous hydroxide with the at least one source of dilute aqueous peroxide to generate at least one source of dilute aqueous peroxide having a pH of greater than 8;

f. Providing at least one source of acyl donor;

g. supplying one or more of the at least one source of acyl donor and at least one source of dilute aqueous peroxide having a pH of greater than 8 to a mixing coil or mixer that provides sufficient mixing to produce a single-phase composition of non-equilibrium peroxycarboxylic acid.

In an embodiment, the stream of non-equilibrium peroxycarboxylic acid solution is generated by a process comprising:

a. Providing a stream of water;

b. Using a flow controller or pump to regulate the flow rate of the stream of water;

c. Providing a source of aqueous hydroxide;

d. Diluting a stream of the aqueous hydroxide by mixing it with water from the water stream;

e. Providing a source of aqueous peroxide;

f. Mixing a stream of the aqueous peroxide with the stream of diluted hydroxide so that the combined stream has peroxide concentration less than 10% (w/w), and a pH between 10-13.5;

g. Providing a source of acyl donor;

h. Mixing the stream of diluted peroxide with pH greater than 8 with a stream of the acyl donor in a mixing coil or mixer that provides sufficient mixing to produce a single phase solution comprising non-equilibrium peroxycarboxcylic acid at its outlet.

In further embodiments, the at least one feed stream comprising a non-equilibrium peroxycarboxylic acid has a concentration below 5.6%, and a source of water is used to dilute one or more of the at least one feed stream comprising a non-equilibrium peroxycarboxylic acid, the source of aqueous peroxide, and/or the stream of acid or hydroxide.

In further embodiments, a flow controller or pump regulates the flow rate of one or more of the at least one source of water, the aqueous peroxide source is hydrogen peroxide, the acyl precursor is a liquid acetyl precursor, and the acyl precursor is selected from the group consisting of asacetin, diacetin, triacetin, acetylsalicylic acid, ($\beta$)-D-glucose pentaacetate, cellulose acetate, D-mannitol hexaacetate, sucrose octaacetate, acetic anhydride, N,N,N'N'-tetraacetylethylenediamine (TAED), N-acetyl glycine, N-acetyl-5 DL-methionine, 6-acetamidohexanoic acid, N-acetyl-L-cysteine, 4-acetamidophenol, and N-acetyl-Lglutamine. In a further embodiment, the liquid acetyl precursor is triacetin.

In further embodiments, the aqueous hydroxide source is an alkali metal hydroxide solution or an earth alkali metal hydroxide solution, the aqueous hydroxide source is a sodium hydroxide solution, and the aqueous peroxide source is hydrogen peroxide.

In an embodiment, there is provided a system for on-site and on-demand generation of non-equilibrium solutions of peroxycarboxcylic acids comprising:

a. A stream of water;

b. A flow sensor placed between said water source and the balance of the system;

c. A first container containing a first solution comprising an aqueous peroxide source;

d. A check valve placed between said aqueous peroxide source and the balance of the system that prevents flow of liquid from the balance of the system in the direction of said aqueous peroxide source;

e. A second container containing a second solution comprising an aqueous hydroxide source;

f. A check valve placed between said aqueous hydroxide source and the balance of the system that prevents flow of liquid from the balance of the system in the direction of said aqueous peroxide source;

g. A third container containing a third solution comprising an acetyl precursor;

h. A pipe or tube manifold with an inlet end accepting flows from said water source and said aqueous peroxide source;

i. A first mixer accepting at its inlet end a diluted aqueous peroxide flow from the outlet of said manifold and flow from said aqueous hydroxide source;

j. A first pH probe that measures the pH of the outlet flow from said mixer;

k. A reactor that accepts at its inlet end the flow from the outlet of said static mixer and said acyl precursor;

l. A second pH probe that measures the pH of the outlet flow from said reactor;

m. A fourth container containing a fourth solution comprising an acidic aqueous solution;

n. A second static mixer accepting at its inlet end the outlet flow from said reactor and said acidic aqueous solution;

o. A third pH probe that measures the pH of the outlet flow from said second static mixer;

p. A control system that accepts electrical signals from said mass flow sensor, said first pH probe, said second pH probe, and said third pH probe, and provides electrical signals to control the speed of a first pumping system pumping said aqueous peroxide source, a second pumping system pumping said aqueous hydroxide source, a third pumping system pumping said acetyl precursor; and a fourth pumping system pumping said aqueous acidic solution;

q. A product tank that collects the outlet flow from said mixing coil.

In further embodiments, the control system stops the operation of the first pumping system and the second pumping system if the mass flow sensor indicates flow of water below a predetermined alarm level; the residence time of the stream in the reactor is sufficient for the two phase mixture to form a single phase solution; the acidic aqueous solution is a sulfuric acid solution; and the acidic aqueous solution is an acetic acid solution.

In an embodiment, there is provided a method for producing non-equilibrium peroxycarboxcylic acid comprising:

a. diluting a solution of aqueous hydrogen peroxide with water to a concentration less than 10% (w/w), preferably less than 6% (w/w);

b. adjusting the pH of the solution to between 11.5-13.5 by adding alkali metal hydroxide or alkali earth metal hydroxide, or solutions of alkali metal hydroxide or alkali earth metal hydroxide;

c. adjusting the ratio of peroxide to acetyl group in the hydrogen peroxide solution to at least 1, more preferably 1.5 or greater by adding a suitable O-acetyl or N-acetyl donor;

d. suitably mixing the components for sufficient time to allow complete reaction;

e. optionally adding acid to the reacted mixture to adjust the mixture pH;

f. optionally adding additional peroxide to the reacted mixture to augment the mixture's peroxide component;

g. further diluting the mixture with either clean (softened or DI) water or process water to point-of-use biocide concentration.

In an embodiment, there is provided a method for producing non-equilibrium peroxycarboxcylic acid comprising:

a. diluting the HP feedstock to a concentration less than 10% (w/v);

b. adjusting the pH to 11.5-13.5 by addition of alkali metal hydroxide (preferably NaOH, or KOH) to maximize the ratio of —OOH to —OH in the reaction mixture;

c. optimized the pH to have sufficient alkalinity to result in a product mixture having pH greater than 9 after base-consuming reactions are complete;

d. reacting the diluted, alkaline peroxide solution with a suitable O-acetyl or N-acetyl peroxide activator that is preferably non-toxic, non-flammable, and has kinetically rapid reactivity with peroxide, and preferably is monoacetin, diacetin, or triacetin;

e. controlling the stoichiometry of —OOH to acetyl group to result in high selectivity for PAA production over acetic acid, or alternatively to result in a product mixture with a specified remaining peroxide concentration, which may be desirable for certain applications;

f. controlling the ratio of —OOH to acetyl group to result in a product mixture with a specified remaining concentration of —OOH;

g. adjusting the chemical properties after reaction by augmentation of peroxide, or pH adjustment by addition of acidic components, making the mixture more stable, where acids may preferably include sulfuric acid, acetic acid, citric acid, nitric acid.

In an embodiment, there is provided a method for producing non-equilibrium peroxycarboxcylic acid comprising:

a. diluting aqueous hydrogen peroxide solution with softened or deionized water to a concentration less than 10% (w/w), preferably less than 6% (w/w);

b. adding alkali metal hydroxide or alkali earth metal hydroxide, or solutions of alkali metal hydroxide or alkali earth metal hydroxide to adjust the pH of the resulting peroxide mixture to between 10 to 13.5;

c. adding a suitable O-acetyl or N-acetyl donor such that the ratio of peroxide to acetyl group in the reaction mixture is at least 1, more preferably 1.5 or greater;

d. mixing the components sufficiently and for a sufficient time for the two phase mixture to change into a single phase solution, indicating a nearly complete reaction;

e. optionally adding an acid source to the reacted mixture to adjust the mixture pH;

f. optionally adding additional peroxide to the reacted mixture to augment the mixture's peroxide component.

In an embodiment, there is provided a method for producing non-equilibrium peroxycarboxcylic acid comprising:

a. diluting aqueous hydrogen peroxide solution with a dilute alkali metal hydroxide or alkali earth metal hydroxide solution to produce a mixture with a hydrogen peroxide concentration less than 10% (w/w), preferably less than 6% (w/w) and a pH between 10 and 13.5;

b. adding a suitable O-acetyl or N-acetyl donor such that the ratio of peroxide to acetyl group in the reaction mixture is at least 1, more preferably 1.5 or greater;

c. suitably mixing the components for sufficient time to allow complete reaction;

d. optionally adding additional dilute peroxide (<35% w/w) to the reacted mixture to augment the mixture's peroxide component;

e. optionally adding acid to the reacted mixture to adjust the mixture pH;

f. further diluting the mixture with either clean (softened or DI) water or process water to point-of-use biocide concentration.

In an embodiment, there is provided a process for producing an antimicrobial solution at the point-of-use comprising:

a. first diluting aqueous hydrogen peroxide solution with softened or DI water to a concentration less than 10% (w/w), preferably less than 6% (w/w);

b. secondly adding alkali metal hydroxide or alkali earth metal hydroxide, or solutions of alkali metal hydroxide or alkali earth metal hydroxide to adjust the pH of the resulting peroxide mixture to between 11.5-13.5;

c. thirdly adding a suitable O-acetyl or N-acetyl donor such that the ratio of peroxide to acetyl group in the reaction mixture is at least 1, more preferably 1.5 or greater;

d. suitably mixing the components for sufficient time to allow complete reaction;

e. optionally adding acid to the reacted mixture to adjust the mixture pH;

f. optionally adding additional peroxide to the reacted mixture to augment the mixture's peroxide component;

g. further diluting the mixture with either clean (softened or DI) water or process water to point-of-use biocide concentration.

In an embodiment, there is provided a process for producing an antimicrobial solution at the point-of-use comprising:

a. first diluting aqueous hydrogen peroxide solution with a dilute alkali metal hydroxide or alkali earth metal hydroxide solution to produce a mixture with a hydrogen peroxide concentration less than 10% (w/w), preferably less than 6% (w/w) and a pH between 11.5-13.5;

b. Next adding a suitable O-acetyl or N-acetyl donor such that the ratio of peroxide to acetyl group in the reaction mixture is at least 1, more preferably 1.5 or greater;

c. suitably mixing the components for sufficient time to allow complete reaction;

d. optionally adding additional peroxide to the reacted mixture to augment the mixture's peroxide component;

e. optionally adding acid to the reacted mixture to adjust the mixture pH;

f. further diluting the mixture with either clean (softened or DI) water or process water to point-of-use biocide concentration.

In an embodiment, there is provided a process for continuously producing an antimicrobial solution at the point-of-use comprising:

a. first continuously diluting aqueous hydrogen peroxide solution with softened or DI water to produce a peroxide feed stream with a concentration less than 10% (w/w), preferably less than 6% (w/w)

b. secondly continuously adding alkali metal hydroxide or alkali earth metal hydroxide, or solutions of alkali metal hydroxide or alkali earth metal hydroxide to adjust the pH of the resulting peroxide feed stream to between 11.5-13.5;

c. continuously adding a acetyl donor to a flowing dilute alkaline peroxide feed stream such that the ratio of peroxide to acetyl group is greater than 1:1.

In an embodiment, there is provided a process for continuously producing an antimicrobial solution at the point-of-use comprising:

a. continuously diluting aqueous hydrogen peroxide solution with softened or DI water to produce a peroxide feed stream with a concentration less than 10% (w/w), preferably less than 6% (w/w)

b. continuously adding alkali metal hydroxide or alkali earth metal hydroxide, or solutions of alkali metal hydroxide or alkali earth metal hydroxide to adjust the pH of the resulting peroxide feed stream to between 11.5-13.5;

c. continuously adding a acetyl donor to a high velocity flowing dilute alkaline peroxide feed stream such that the two-phase droplet flow through a reaction mixer maintains a pseudo-excess of peroxide to acetyl group.

In an embodiment, there is provided a process for continuously producing an antimicrobial solution at the point-of-use comprising:

a. continuously diluting aqueous hydrogen peroxide solution with softened or DI water to produce a peroxide feed stream with a concentration less than 10% (w/w), preferably less than 6% (w/w)

b. continuously adding alkali metal hydroxide or alkali earth metal hydroxide, or solutions of alkali metal hydroxide or alkali earth metal hydroxide to adjust the pH of the resulting peroxide feed stream to between 11.5-13.5;

c. continuously adding a acetyl donor to a flowing dilute alkaline peroxide feed stream such that the ratio of peroxide to acetyl group is greater than 1:1;

d. continuously adding acid to the reacted mixture to lower the pH of the product.

In an embodiment, there is provided a process for continuously producing an antimicrobial solution at the point-of-use comprising:

a. continuously diluting aqueous hydrogen peroxide solution with softened or DI water to produce a peroxide feed stream with a concentration less than 10% (w/w), preferably less than 6% (w/w)

b. continuously adding alkali metal hydroxide or alkali earth metal hydroxide, or solutions of alkali metal hydroxide or alkali earth metal hydroxide to adjust the pH of the resulting peroxide feed stream to between 11.5-13.5;

c. continuously adding a acetyl donor to a flowing dilute alkaline peroxide feed stream such that the ratio of peroxide to acetyl group is greater than 1:1;

d. continuously adding aqueous peroxide to the reacted mixture to augment the concentration of peroxide in the resulting biocide mixture.

In an embodiment, there is provided a process for minimizing product decomposition by continuous production of an antimicrobial solution reacting dilute peroxide with an inorganic base solution and an acetyl donor such that the concentration of the peroxide feed is maintained below 10% (w/w), the pH is maintained between 11.5-13.5, and the acetyl donor is maintained at ratio of greater than 1:1 during the process.

In an embodiment, there is provided a process for continuously producing a non-hazardous antimicrobial solution at the point-of-use by reacting dilute peroxide stream with an inorganic base and an acetyl donor such that the concentration of peroxide is maintained below 10% and the concentration of peroxyacid produced is maintained below 5%.

In an embodiment, there is provided a process for the continuous high-yield production of a biocide mixture by reacting a dilute peroxide feed stream with an acetyl donor such that that the pH of the reaction mixture is maintained at the point of maximum difference between the concentration of $^-OOH$ and the concentration of $^-OH$.

In an embodiment, there is provided a biocide composition comprising:

a. aqueous hydrogen peroxide (or an aqueous source of hydrogen peroxide)

b. alkali metal or alkali earth metal hydroxide or solutions of alkali metal hydroxide or alkali earth metal hydroxide and c. O-acetyl or N-acetyl donor, or solutions of O-acetyl or N-acetyl donors d. water wherein the aqueous hydrogen peroxide, water, alkali metal hydroxide are mixed prior to addition of the acetyl donor such that the initial concentration of peroxide is between 0.04-10% (w/w) in the mixture, the initial pH of the mixture is between 11.5 and 13.5. Wherein the acetyl donor is then mixed such that the ratio of peroxide to acetyl group is at least 1 and more preferably 1.5.

In an embodiment, there is provided a biocide composition comprising (by weight percentage): 0.04-10% aqueous hydrogen peroxide solution, 0.01 to 10% triacetin, 0.01 to 3% sodium hydroxide and water.

In an embodiment, there is provided a biocide composition comprising (by weight percentage): 0.04-10% aqueous inorganic peroxide solution, 0.01 to 10% acetyl donor, 0.01 to 3% inorganic base and water.

In an embodiment, there is provided a liquid biocide composition comprising:

a. between 0-5% PAA b. between 0.04-40% peroxide c. between 0-3% alkali metal hydroxide d. between 0.01-10% acetic acid e. between 0-5% glycerol, or other byproduct.

The system controls flow rates and proportions of feedstocks/reactants, performs the required sequence of reaction steps to produce high yield peroxycarboxcylic acid solutions in a continuous manner, and provides optimal reaction time and reactant mixing for continuous and safe on-site production.

In various embodiments, system features include:

a. maintaining described sequence of steps b. preventing any dangerous mixtures of incompatible feedstocks in the system or in secondary containment c. maintaining optimal dilution of HP feed stream.

d. maintaining optimal reaction mixture pH by proportional alkali feed stream flow e. maintaining specified ratio of peroxide to acyl group (peroxide to triacetin stoichiometry)

f. providing optimal reaction time for high yield PAA product g. providing optimal mixing of heterogeneous reaction mixture h. providing optimal 'plug flow' reaction mixture for enhanced yield i. providing sufficient day tank (buffer tank) to allow for product delivery during periods of system maintenance j. optionally providing stream of treated, or clean process water In various embodiments, dilution includes less than 10% (w/w) aqueous HP, less than 6% (w/w) aqueous HP, less 3.5% (w/w) aqueous HP, between 1% and 5% (w/w) aqueous HP, and between 0.1% and 5% (w/w) aqueous HP.

In various embodiments, ratios include greater than 1-fold excess peroxide to acyl group, greater than 1.5 fold excess peroxide to acyl group, greater than 2.0 fold excess peroxide to acyl group, and greater than 1-fold and less than 2-fold excess peroxide to acyl group.

Acyl donors that may be used with this device include N-acetyl and O-acetyl donors. O-acetyl donors that may be used include, but are not limited to, monoacetin, diacetin, triacetin, and acetylsalicylic acid.

Plug flow in the mixer provides the conditions for fastest reaction time to produce peroxycarboxcylic acids, which is important for on-demand production. Plug flow conditions will exist in the mixer when the flow rate of the stream and volume of the mixer create conditions that minimize backflow for a given volume of the stream.

The water stream may be municipal water, softened municipal water, or deionized water.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Molecules disclosed herein may contain one or more ionizable groups, groups from which a proton can be removed (e.g., —COOH) or added (e.g., amines) or which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice embodiments of the invention, unless otherwise stated. One of ordinary skill in the art will appreciate that starting materials, catalysts, reagents, synthetic methods, purification methods, analytical methods, and assay methods, other than those specifically exemplified can be employed in the practice of embodiments of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of embodiments of the invention claimed. Thus, it should be understood that although embodiments of the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

Whenever a range is given in the specification, for example, a temperature range, a time range, a pH range, a composition or concentration range, or an amount, concentration, or other value or parameter given as a range, preferred range, or a list of upper preferable values and lower preferable values, all intermediate ranges and subranges, as well as all individual values included in the ranges given are intended to be included in the disclosure. This is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of embodiments of the invention be limited to the specific values recited when defining a range. The upper and lower limits of the range may themselves be included in the range. It will be understood that any subranges or individual values in a range or subrange that are included in the description herein can be excluded from the claims herein.

All patents and publications mentioned in the specification are indicative of the levels of skill of those skilled in the art to which embodiments of the invention pertains. Unless otherwise stated, references cited herein are incorporated by reference herein in their entirety to provide the reader with a more complete background and it is intended that this information can be employed herein, if needed, to exclude specific embodiments that are in the prior art. The references are not to be construed as an admission that such references constitute prior art for patentability determination purposes.

What is claimed is:

1. A method for producing non-equilibrium peroxycarboxylic acid solution having a controlled ratio of peroxycarboxylic acid to peroxide and a controlled pH, the method comprising:
   a. providing at least one feed stream comprising a non-equilibrium peroxycarboxylic acid, the feed stream having a preselected volumetric flow rate;
   b. supplying at least one source of aqueous peroxide at a preselected volumetric flow rate to the at least one non-equilibrium peroxycarboxylic acid feed stream;
   c. supplying at least one source of acid or hydroxide at a preselected volumetric flow rate to the at least one non-equilibrium peroxycarboxylic acid feed stream and/or the at least one source of aqueous peroxide;
   d. varying the volumetric flow rates of the at least one non-equilibrium peroxycarboxylic acid feed stream, the at least one source of aqueous peroxide, and the at least one source of acid or hydroxide, whereby the ratio of peroxycarboxylic acid to peroxide and the pH of the non-equilibrium peroxycarboxylic acid solution are each selectively controlled to a desired value.

2. The method of claim 1, wherein the at least one non-equilibrium peroxycarboxylic acid feed stream has a peroxide concentration below 5.6%.

3. The method of claim 1, wherein a source of water is used to dilute the at least one non-equilibrium peroxycarboxylic acid feed stream, the source of aqueous peroxide, and/or the stream of acid or hydroxide.

4. The method of claim 1 in which the at least one non-equilibrium peroxycarboxylic acid feed stream is generated by a process comprising:
   a. providing a stream of water;
   b. using a flow controller or pump to regulate the flow rate of the stream of water;
   c. providing a source of aqueous hydroxide;
   d. diluting the aqueous hydroxide source by mixing it with water from the water stream;
   e. providing a source of aqueous peroxide;
   f. mixing the source of the aqueous peroxide with the diluted hydroxide forming a combined solution thereof having a peroxide concentration less than 10% (w/w), and a pH between 10-13.5;
   g. providing a source of acyl donor;
   h. mixing the source of diluted peroxide with pH greater than 8 with a stream of the acyl donor in a mixing coil or mixer; and
   i. mixing the diluted peroxide and the acyl donor to produce a single phase solution comprising non-equilibrium peroxycarboxylic acid at its outlet.

5. The method of claim 4, wherein the aqueous hydroxide source is an alkali metal hydroxide solution or an earth alkali metal hydroxide solution.

6. The method of claim 4, wherein the aqueous hydroxide source is a sodium hydroxide solution.

7. The method of claim 4, wherein the aqueous peroxide source is hydrogen peroxide.

8. The method of claim 4, wherein the acyl donor is a liquid acetyl donor.

9. The method of claim 8, wherein said liquid acetyl donor is triacetin.

* * * * *